United States Patent [19]
Ørum et al.

[11] Patent Number: 6,020,132
[45] Date of Patent: Feb. 1, 2000

[54] METHOD OF ANALYSIS USING SIGNAL AMPLIFICATION

[75] Inventors: Henrik Ørum, Vorlose; Troels Koch, Kobenhaven; Martin Borre, Hedehusene; Henrik Frydenlund Hansen, Rodovre, all of Denmark

[73] Assignee: Roche Diagnostics GmbH, Mannheim, Germany

[21] Appl. No.: 08/993,303

[22] Filed: Dec. 18, 1997

[30] Foreign Application Priority Data

Dec. 21, 1996 [WO] WIPO ................................. 96120730

[51] Int. Cl.⁷ .............................. C12Q 1/68; C12P 19/34; C07H 21/04
[52] U.S. Cl. ........................... 435/6; 435/91.1; 536/24.3; 536/24.31; 536/24.32
[58] Field of Search ............................ 435/6, 91.1, 91.2; 536/24.3, 24.31, 24.32, 24.33

[56] References Cited

U.S. PATENT DOCUMENTS 5,437,977  8/1995  Segev et al. ................................. 435/6

FOREIGN PATENT DOCUMENTS 0 317 077   5/1989  European Pat. Off. .
WO96/36734  11/1996  WIPO .

OTHER PUBLICATIONS

International Publication No. WO 95/14706 published Jun. 1, 1995.
International Publication No. WO 95/08556 published Mar. 30, 1995.
International Publication No. WO 95/01370 published Jan. 12, 1995.
International Publication No. WO 95/08000 published Mar. 23, 1995.
International Publication No. WO 95/01365 published Jan. 12, 1995.
International Publication No. WO 95/01370 published Jan. 12, 1995.
International Publication No. WO 95/14706 published Jun. 1, 1995.
International Publication No. WO 92/11390 published Jul. 9, 1992.
International Publication No. WO 95/20320 published Aug. 3, 1995.

Ito et al., *Proc. Natl. Acad. Sci. USA,* vol. 89, pp. 495–498, Jan. 1992, "Sequence–Specific DNA purification by triplex affinity capture".

*Primary Examiner*—Kenneth R. Horlick
*Assistant Examiner*—Jeffrey Siew
*Attorney, Agent, or Firm*—Nikaido Marmelstein Murray & Oram, LLP

[57] ABSTRACT

A method for determining a molecule A comprising a sample of molecules capable of participating in formation of triplex structures is useful for sensitive determination. The principle can be used to determine any kind of analytes.

23 Claims, 13 Drawing Sheets

DNA: SA, C1, C2
PNA: B1, B2

DNA: SA, B1, B2, D1, D2
PNA: C1, C2, E1, E2

DNA: SA, C1, C2
PNA: B1, B2

FIG.2
DEFINITIONS:
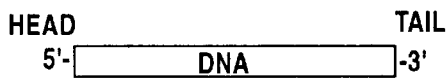   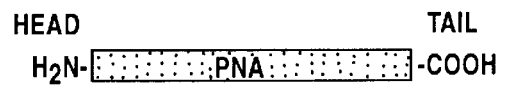
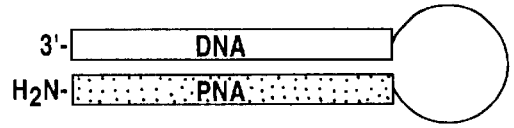  A  ANTI-PARALLEL, "HEAD TO TAIL"
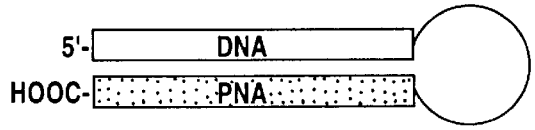  B  ANTI-PARALLEL, "TAIL TO HEAD"
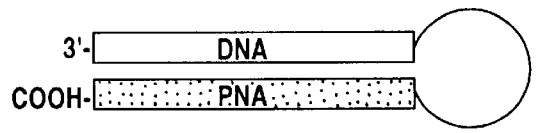  C  PARALLEL, "HEAD TO HEAD"
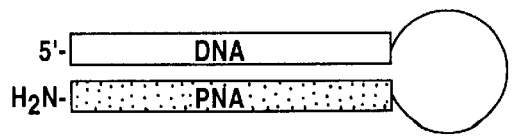  D  PARALLEL, "TAIL TO TAIL"

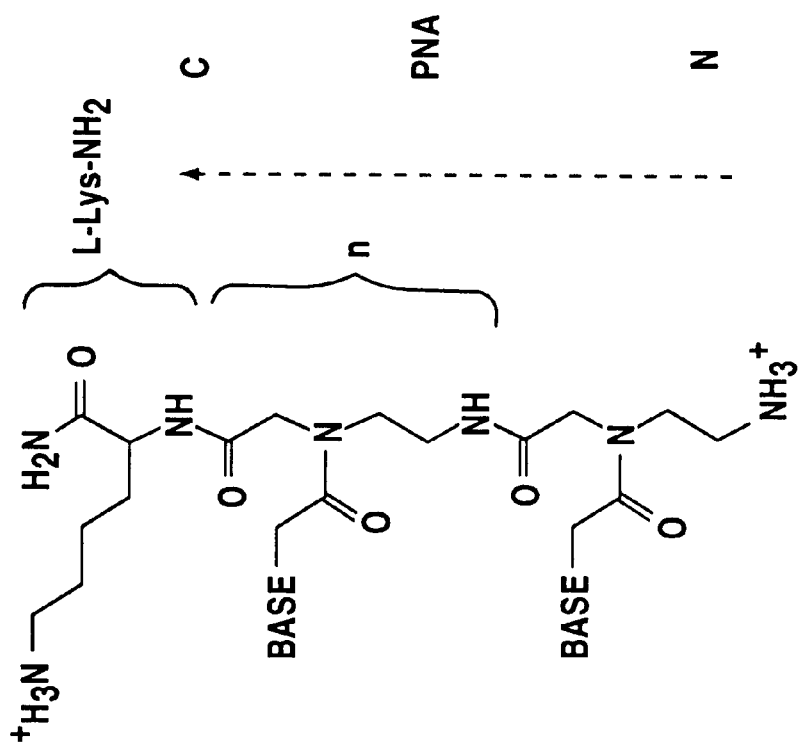
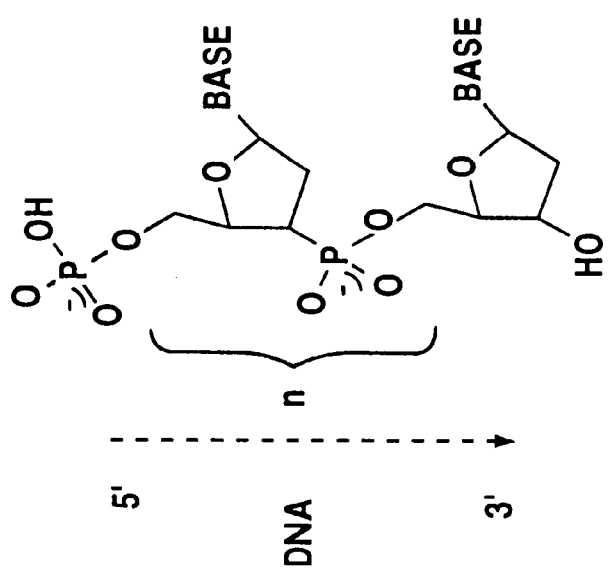
FIG.4

FIG.7

```
       C                                    D
              TTCCTT T T TC - AAAAGAGAAAA
    TTTTCTCTTTT - AAGGAAAAAG
              TTCCTT T T TC - AAAAGAGAAAA
                                            D
```

FIG.8

HOOC-[ PNA ]- NH-LINKER-HN-[ PNA ]-COOH

FIG. 9

COOH-[ PNA ]-NH₂ WATSON-CRICK

5'-[ DNA ]-3'

H₂N-[ PNA ]-COOH HOOGSTEEN

```
                          SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Oligodeoxyribonucleotide"

(ix) FEATURE:
         (A) NAME/KEY: misc_feature
         (B) LOCATION: 1
         (D) OTHER INFORMATION: /note= "AT THE TERMINUS IS AN
             AMINOHEXYL ALKYLATED GROUP"

(xi) SEQUENCE DESCRIPTION: SEQ ID NO:1:

AAAGAAGAAA                                                              10

(2) INFORMATION FOR SEQ ID NO:2:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "OLIGODEOXYRIBONUCLEOTIDE"

(ix) FEATURE:
         (A) NAME/KEY: misc_feature
         (B) LOCATION: 1
         (D) OTHER INFORMATION: /note= "AT THE TERMINUS IS AN
             AMINOHEXYL ALKYLATED GROUP"

(xi) SEQUENCE DESCRIPTION: SEQ ID NO:2:

AAGAGAAAAA                                                              10

(2) INFORMATION FOR SEQ ID NO:3:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "OLIGODEOXYRIBONUCLEOTIDE"

(xi) SEQUENCE DESCRIPTION: SEQ ID NO:3:

CGACTTCAGC ATGACTCAAA GAAGAAA                                           27

(2) INFORMATION FOR SEQ ID NO:4:

(i) SEQUENCE CHARACTERISTICS:
         (A) LENGTH: 27 base pairs
         (B) TYPE: nucleic acid
         (C) STRANDEDNESS: single
         (D) TOPOLOGY: linear
```

-continued

```
    (ii) MOLECULE TYPE: other nucleic acid
        (A) DESCRIPTION: /desc = "OLIGODEOXYRIBONUCLEOTIDE"

(xi) SEQUENCE DESCRIPTION: SEQ ID NO:4:

ATGTGGACAT TGTCATCAAG AAAAGAA                                            27
```

METHOD OF ANALYSIS USING SIGNAL AMPLIFICATION

FIELD OF THE INVENTION

The present invention relates to chimeric nucleic acids compounds that have the capacity of forming triplex structures, to the production and purification of such chimeric compounds, and to their use in signal amplification techniques.

BACKGROUND OF THE INVENTION

Detection and quantification of nucleic acid molecules constitutes a fundamental trait in several diagnostic techniques. However, the amount of accessible nucleic acid target molecules in a specific sample is in general low, and direct hybridization with a polynucleotide probe therefore in many cases insufficient for detection. In the case of an infectious organism, the classical solution has been enrichment by culturing, but this is time-consuming and therefore unsuitable for rapid diagnosis. A way to circumvent these problems is to amplify the target molecule. This can be accomplished in one of several ways, for example polymerase chain reaction (PCR, as it is described in U.S. Pat. No. 4,683,195 or EP-A-0 630 971), ligase chain reaction (LCR, EP-A-0 320 308) or NASBA (EP-A-329 822). However, all of these techniques utilize enzymes for amplification of target nucleic acid molecules and, consequently, they suffer from the drawback that compounds in the sample specimen may inhibit these enzymes. Therefore, current protocols based on these techniques often include laborious sample preparation steps such as, for example purification and concentration of DNA. Furthermore, when the target sequence is amplified the risk of contamination becomes significantly increased. Several methods have been described to overcome contamination problems, including 1) digestion with nucleases that specifically degrades nucleic acid molecules that have been produced during previous analysis (EP-A-0 401 037); and 2) special laboratory practice that minimises carry over between new samples and previously analysed material. However, methods for avoiding contamination and inhibition are in general costly and cumbersome.

Another solution for signal amplification would be to employ a method in which the number of signal-producing compounds is increased. Such methods have been described by for example EP-A-0 317 077, WO 95/01365 and WO 95/08000. These techniques utilize multi-valent intermediate probes containing a large amount of identical nucleotide sequences bound covalently to each other and each intermediate probe being capable of hybridizing with up to 50 signal producing secondary probes simultaneously. However, these techniques utilize large molecules as intermediate probes which results in less favorable kinetics.

Thus, it would be highly desirable to have a method for signal amplification which is rapid, simple, sensitive, based on stable compounds and on non-enzymatical reactions.

SUMMARY OF THE INVENTION

Subject of the invention is therefore a method of determining a molecule A containing a sequence SA of nucleobases, said molecule being capable of forming a triple helix structure through said sequence SA comprising providing a reaction mixture containing multiple probe molecules B containing a first segment B1 capable of participating in a triple helix structure with A through sequence SA and a segment B2 that allows for direct or indirect detection, incubating said reaction mixture at conditions allowing the formation of triple helices and determining the formation of triple helices using said segment B2.

A further subject of the invention is a molecule especially advantageous for this method.

A further object of the invention is a method for the determination of an analyte using the above mentioned method for determining a molecule A.

A further object of the invention is the use of multiple triple helix structures (triplex structures) for the determination of an analyte.

BRIEF DESCRIPTION OF THE DRAWINGS

In FIG. 2 several ways to link probe segments are given. In the case of the segments comprising DNA and PNA formation of an intramolecular duplex is favored in case A and B. This means that cases C and D are preferred arrangements for forming triple helix structures. FIG. 2 contains the nomenclature used throughout the specification for the arrangement and orientation of strands.

FIG. 4 shows schematically the structure of an exemplified PNA while bound to DNA in the preferred antiparallel mode. It further shows that nucleic acid analogues can be modified by the attachment of groups improving the solubility of the probe, in case of PNA the addition of a lysine residue.

FIG. 7 shows a sequence and binding mode of one molecule of probe C and two molecules of probe D, wherein the second segment of probe D can bind the first segment of probe C.

FIG. 8 shows schematically a probe molecule containing two PNA segments, the amino ends being bound together covalently by a linker moiety L.

FIG. 9 shows the mode in which two PNA molecules bind to one strand of DNA.

DETAILED DESCRIPTION OF THE INVENTION

Figure 1A:
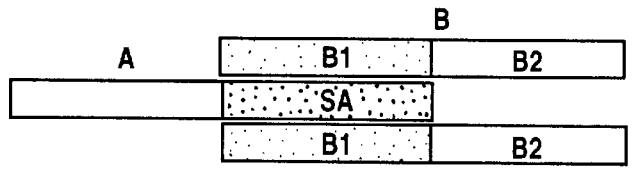
FIG. 1A is a schematic illustration of structures formed from molecules A and probes B.
Figure 1A:
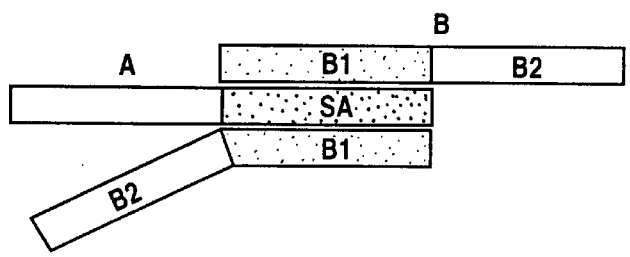
Figure 1A:
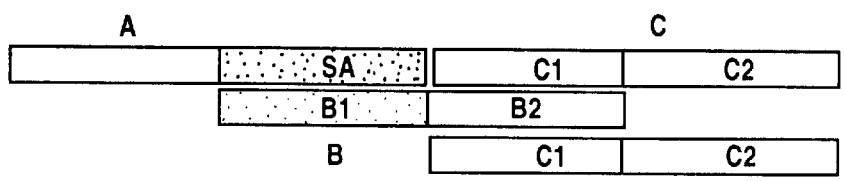
Figure 1A:
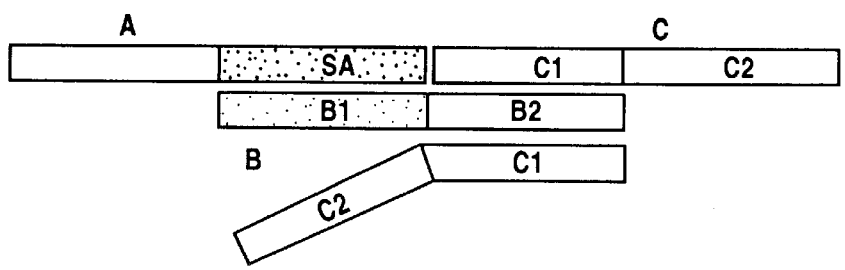
Figure 1A:
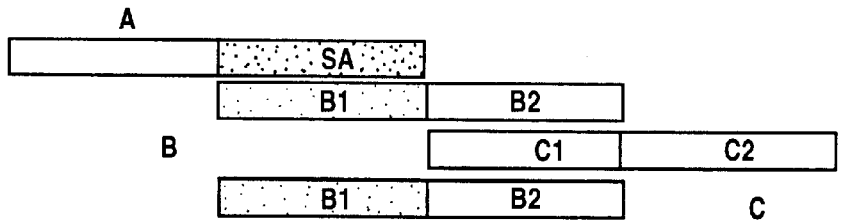
Figure 1B:
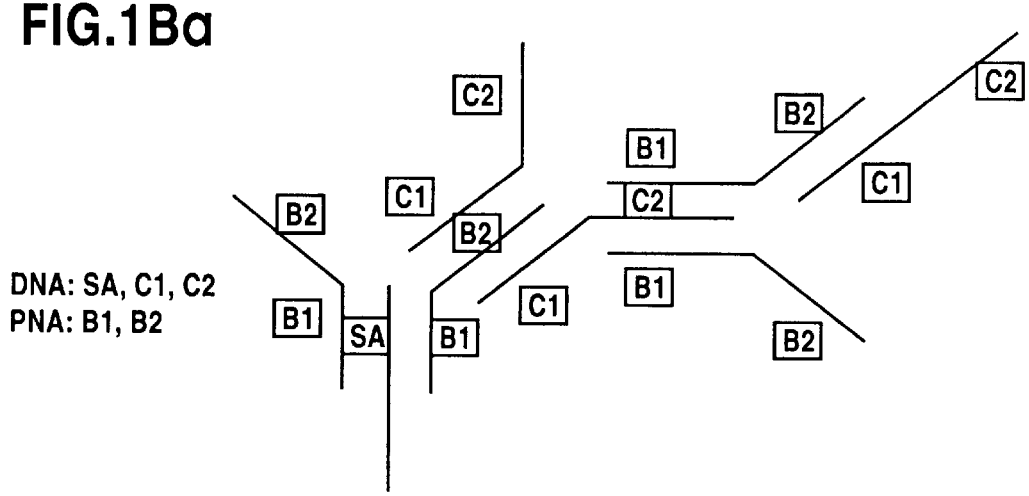
FIG. 1B is a schematic illustration of structures showing how the structures of FIG. 1A can be extended further.
Figure 1B:
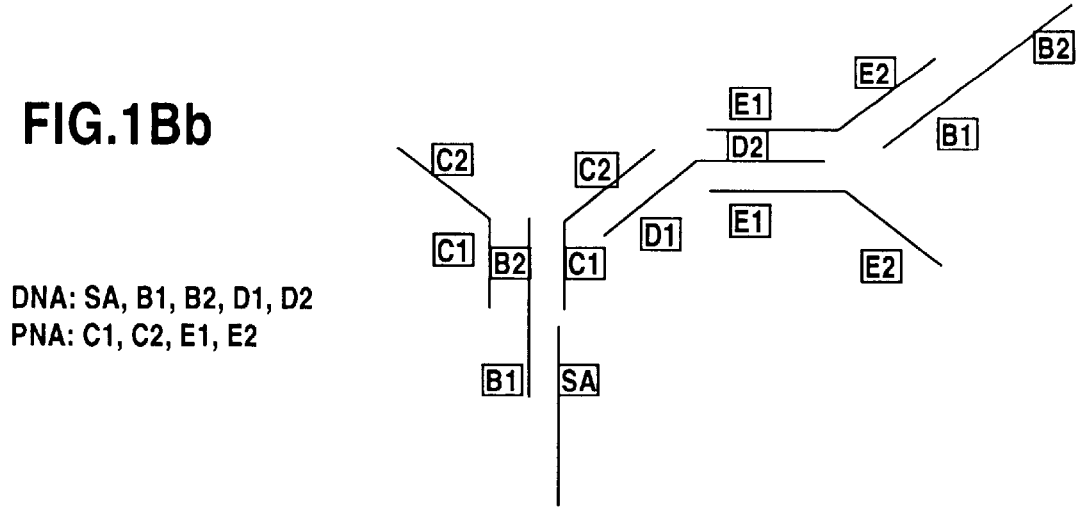
Figure 1B:
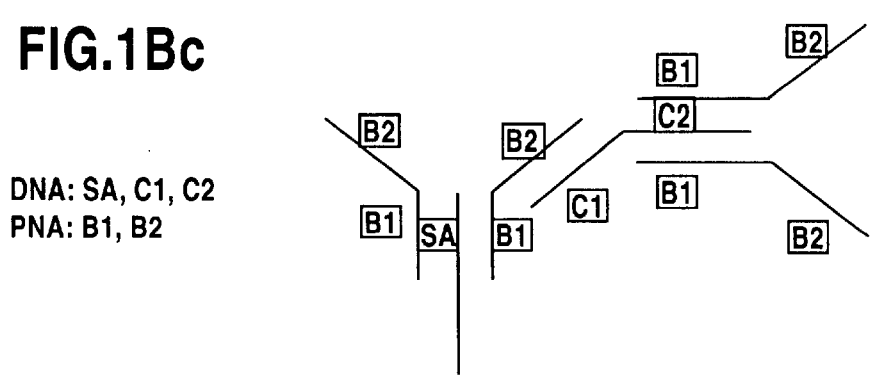

A molecule A can be any moiety containing a sequence SA of nucleobases which sequence is preferably a least 9 bases long, most preferably is between 10 and 30 bases long. The nucleobases are preferably covalently linked in a linear manner to a backbone, especially in a way such that the molecule can bind by base pairing to a nucleic acid containing a sequence of bases complementary to the sequence of bases contained in molecule A. Examples of molecules A are nucleic acids, like RNA, DNA or derivatives thereof and nucleic acid analogues. In very preferred manner the nucleic acid is DNA. Molecule A can also be a molecular moiety, for example a protein or hapten to which a nucleic acid or nucleic acid analogue sequence is attached.

A can be a molecule originating from a sample wherein the presence, absence or amount of this molecule is intended to be determined and analyzed in presence/absence or/and amount, but molecule A can also be a probe or probe unit that is itself intended to be used for the determination of an analyte. Generally the intention behind the occurrence or use of the sequence SA in molecule A is to increase the number of binding sites for labels or the number of labels attached or attachable to molecule A. Therefore the origin and function of the part of molecule A not participating in amplifying a signal can be chosen according to the specific task to be solved. Further the amount of molecule A can be unknown, for example in methods for determining molecule A as an analyte in a sample, or it can be known, for example if a defined amount of molecules A is added to a sample, especially for determining an analyte (for example antigens, antibodies, haptens etc.) different from molecule A.

Sequence SA can contain natural nucleobases, like A, C, G, T and U, or non-natural bases, like 7-deaza-G and mixtures. The important feature of sequence SA is that it has the ability to bind a probe molecule B by base pairing.

A triple helix structure or triplex structure is composed of three strands of molecules, each containing a nucleobase sequence capable of base pairing. Preferably the mode of binding between the three strands involves both Watson/Crick and Hoogsteen base pairing. The formation of triple helix structures requires a high degree of complementarity of the sequence of two of the strands involved to the third strand. In preferred triple helix structures two of the strands are composed of pyrimidine nucleobases of any sequence while the third strand is composed of the complementary purine nucleobase sequence. The triple helical structure therefore preferably has a length of at least six purine or six pyrimidine nucleobases respectively.

It has been shown in WO 95/01370 that peptide nucleic acids (PNAs) have the ability to form triplex structures with nucleic acids. Criteria for forming triple helices can therefore be taken from this patent application. PNAs and their synthesis are disclosed in WO 92/20702 and WO 94/25477. In one embodiment the backbone of PNAs is composed of repeating units of ethylaminoglycine moieties, wherein the nucleobases are bound to the glycine amino group. PNAs in this definition therefore contain an amino terminus (—NH2) and a carboxylic acid terminus (—COOH). These termini can be modified by the attachment of other moieties or the omission of groups (for example the linkage to groups increasing solubility, like lysine).

In FIG. 2 there are shown four possible cases of intramolecular base pairing between a DNA and PNA part of one probe molecule. Prerequisite to FIG. 2 is that the PNA and the DNA part are able to hybridize by base pairing. It becomes clear that the way of linking the PNA sequence to a DNA sequence as shown in FIGS. 2C and 2D is favored over the embodiments shown in FIGS. 2A and 2B. Case 2C and 2D are referred to as parallel binding. In case A the 5' terminus of the DNA (head) is bound to the carboxyl end of the PNA (tail). For forming triple helix structures, the antiparallel arrangement of the sequences should therefore be avoided, the parallel arrangement should be preferred.

Figure 3:
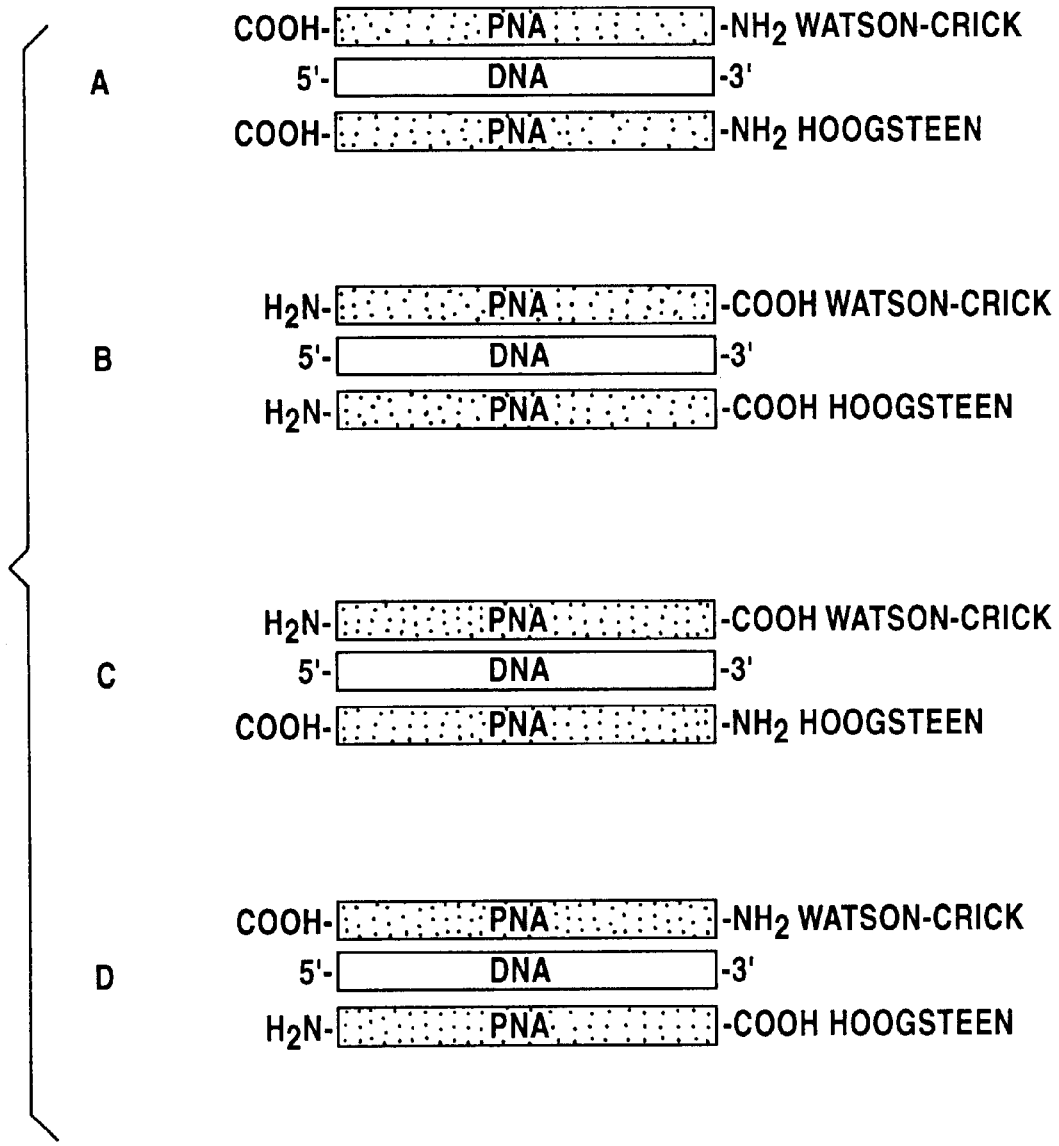
In FIG. 3 four possible orientations for triple helical structures are given. The arrangement in FIG. 3A and 3D are the most preferred.

In FIG. 3 four cases for arranging the three strands of a hypothetical triple helix structure are shown. Again a prerequisite is an ability to hybridize by base pairing of the segments as pointed out above. For the present invention it has been shown that the arrangement according to case B and C should be avoided in order to receive stable triplex structures. Cases A and D are preferred. These cases may be realized by appropriately choosing the nucleobase sequence of the molecules involved.

A probe according to the invention is an entity used for binding a label of any kind to a molecule to be determined. This binding may be direct or indirect.

An assembly of the present invention is defined to contain at least one, preferably just one, molecule A and a multiplicity of different identical probe molecules, preferably more than 2 and most preferably between $10^3$ and $10^7$ probe molecules.

Each probe molecule B is defined to contain at least two segments. They are named in the following as B1 and B2. These segments are preferably and most practically linked together covalently, either directly or indirectly via a linker moiety. It will become apparent from the detailed description of the invention, that the linkage of the two segments must essentially fulfill the purpose to fix the arrangements/orientation of the segments within each probe molecule and to space the regions between B1 and B2. The linker moiety L therefore may have the function to provide a chemical entity for connecting the termini of the segments, but may further have the function to provide a defined distance between the segments to be linked. Linker moieties according to the invention are bivalent moieties of 1 to 100 atoms or more. Typical linker moieties are alkylene groups, dicarboxylic acid moieties, diamine moieties ties or amino acid moieties. Preferred distance is between 20 and 100 atoms, counted between the atoms following the first non-base atom of adjacent bases. One example of a probe molecule is shown in FIG. 8. In this schematic presentation two PNA molecules, each having an amino and a carboxyl terminus are linked together by a linker moiety L, connecting two amino termini of the PNAs. Carboxylic acid termini of PNAs can for example be connected by the use of conventional condensing agents like diimides, for example 1-(3-dimethylaminopropyl)-3-ethyl carbodiimide (EDC). Rigid linkers are further advantageous to avoid intramolecular hybridization.

In case of a probe molecule containing a PNA and a DNA segment preferred linking moieties connect hydroxyl groups of the DNA segment with either of the amino or carboxyl end of the PNA segment (compare FIG. 2). Molecules containing segments of nucleic acids and nucleic acid analogues are described in WO 95/08556 and WO 95/14706. These chimerical molecules can be used in the present invention as probe molecules. At least one of the segments of the probe molecule is capable of participating in a triple helix structure. This segment is therefore preferably designed to consist of a sequence of nucleobases complementary to sequence SA of the molecule A.

By complementarity according to the invention there is meant more than 90% complementarity of a consecutive number of nucleobases of a length of at least nine bases. Complementarity is judged by hydrogen bonding between bases.

While segment B1 is designed for binding to molecule A, segment B2 is designed to minimize binding by base pairing to segment B1 of the same probe molecule (intramolecular binding). Therefore the arrangements of FIGS. 2C and 2D should be chosen. One further way to avoid intramolecular binding is by choosing a linker length, preferably small enough to sterically hinder such binding.

Conditions for formation of triple helical structures may vary dependent upon the kind of moieties making up sequence SA and segment B1. For PNAs and DNA the reaction conditions are described in WO 95/01370. These conditions can be applied for binding of molecule B to molecule A. Preferred these conditions include a pH less than 7, conferring protonation of cytosine molecules. For triple helical structures made up by other strands, a man skilled in the art can determine the optimal conditions for triplex formation by titration experiments or by comparing melting curves and association curves.

The triple helix structure formation reaction is allowed to proceed as long as required to form as much triple helices as intended which will generally be within 1 min. and 12 hours, preferably between 15 and 30 min. Generally, in a way to also estimate the amount of molecules A in the reaction mixture, for example in a quantitative assay, one would stop the reaction after a defined reaction time. Such stopping the reaction can be made by changing the pH such that no further triplex formation can occur. Therefore the pH is changed to more basic conditions, preferably to a pH of more than 8

The formation of triple helices is determined using segment B2 bound to molecule A, as a measure for the presence, absence or amount of molecule A. There are many ways to determine segment B2, depending upon the molecular structure of this segment. In a first instance segment B2 can be determined using its sequence of nucleobases. This sequence makes possible the use of further probes comprising a nucleobase sequence complementary to the sequence of segment B2.

In one embodiment, determination of segment B2 is by a probe containing a sequence complementary to segment B2 and a reporter group. Reporter groups are generally known as moieties that are itself detectable or can be detected by coupling to a detectable moiety. Examples of reporter groups are fluorescent moieties, like fluorescein, and enzymes, for example, peroxidase, or immunologically active substances, like haptens, for example, digoxigenin or colored substances, like rhodamine, or vitamins, like biotin. This labeled probe will be termed secondary probe in the following. The secondary probes preferably do not contain a further nucleobase sequence complementary to a sequence contained in the reaction mixture and therefore are designed to stop the process of adding more probe molecules to molecule A.

The secondary probe can be added at any time to the reaction mixture or even to one of the reagents of the reaction. In a first embodiment, wherein the secondary probe is used as a blocker for the binding of further probe molecules, the secondary probe is added to the reaction mixture at the start of the incubation. The amount of secondary probe must be chosen such that it still allows enhancing the number of binding sites (for example B2) bound to molecule A, but also consecutive binding to a ratio of these binding sites. Therefore generally the amount of secondary probes will be less than the amount of probe molecules B. Secondary probes can further be used to control the level of amplification.

In a second embodiment the secondary probe is added to the reaction mixture after or before the incubation in order to stop the reaction. In this case the amount of the secondary probe is chosen such that it exceed the amount of free segments B2 likely be created during the incubation. This amount will depend upon the amount of molecules A contained in the mixture, the amount of probe molecules added to the mixture and the length of the incubation time.

The molecule A may then be determined via the label present in the secondary probe. This determination is performed analogously to the methods known in the art for these labels. The determination will preferably include calibration of the system by performing the identical reaction sequence for a reaction mixture containing known amounts of molecule A.

The present invention generally makes use of the idea that the formation of triple helix structures allows the formation of branched structures and thereby the formation of multiple sites for binding labels. The more probe molecules are assembled on one molecule A, the more binding sites are created. Using this principle there are various possibilities to assemble probes using the formation of triple helix structures, depending upon the nature of each of the two segments constituting the probe molecules. According to the invention it is possible to use only one kind of probe molecule, but it is also possible to combine different kinds of probe molecules. While the first approach will have the advantage that it is not necessary to synthesize probe molecules of different sequences, the second approach may have the advantage of the possibility to better adapt the assembling reaction to specific requirements. In the following there will be described one embodiment of each approach.

Figure 10:
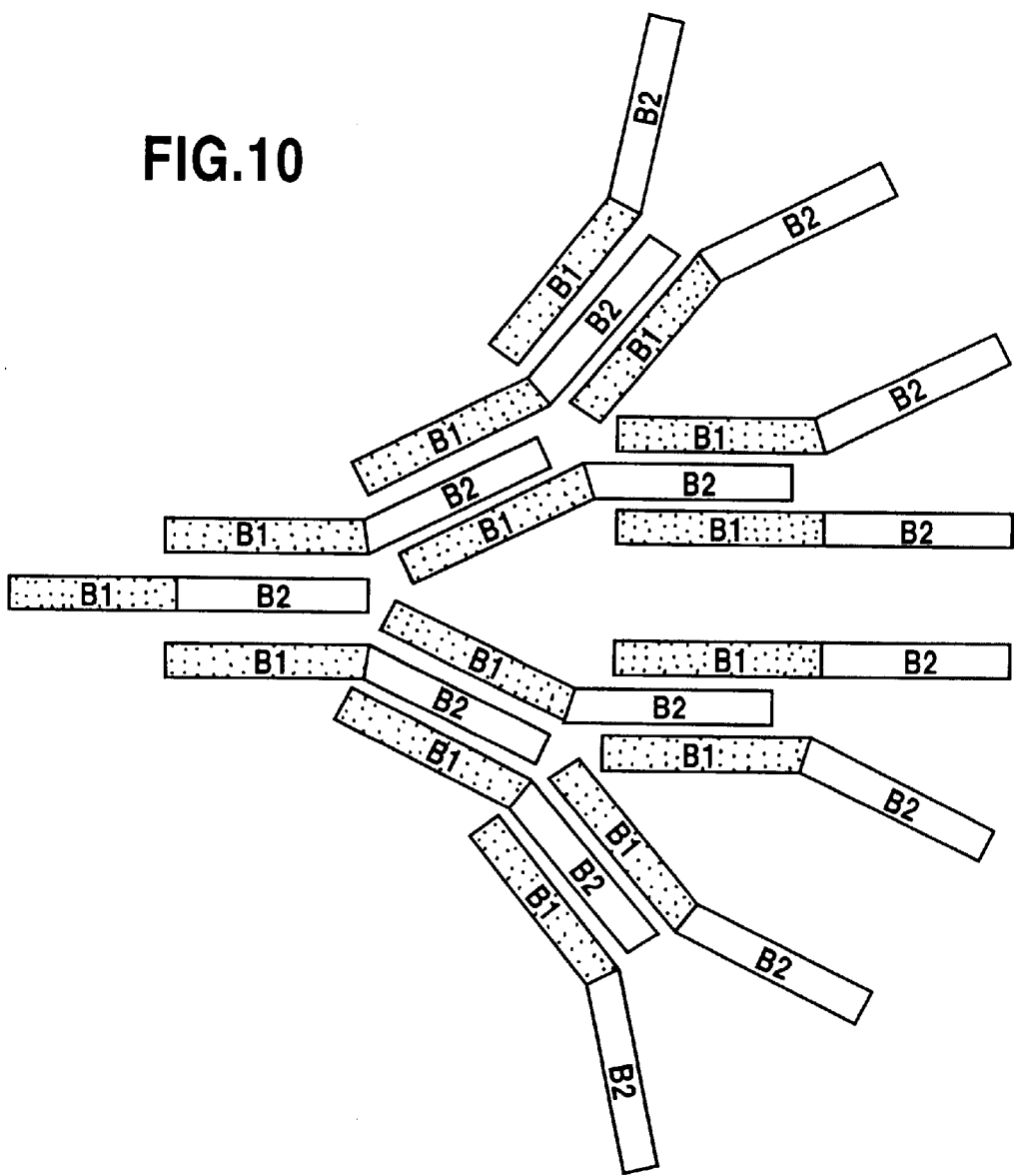
FIG. 10 shows an assembly containing only one molecule B. In this case, B1 is PNA and B2 is nucleic acid.
Figure 11:
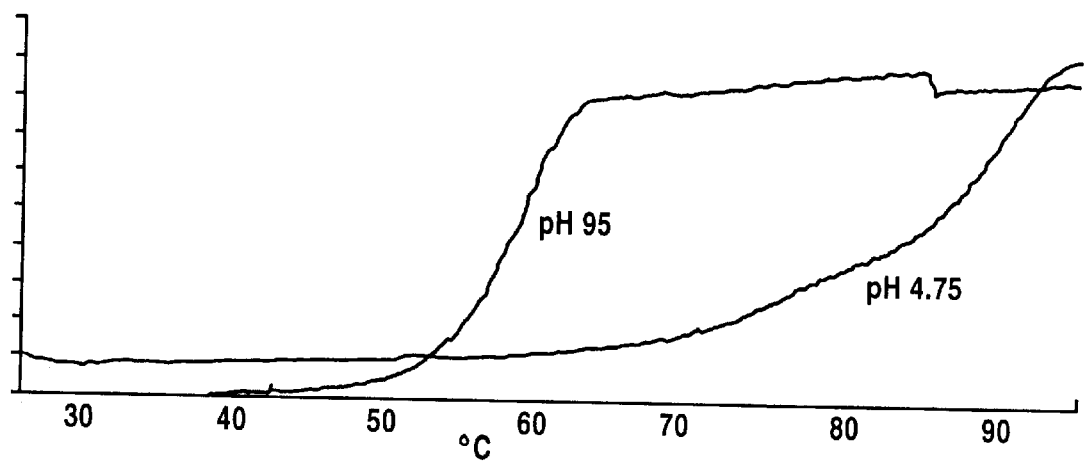
FIG. 11 shows the melting curves of complexes formed between the oligos of example 1 (denoted B1 and C2), measured at pH 4.75 and pH 9.5.

In a first embodiment only one kind of probe molecule is used. This probe molecule therefore constitutes probe molecule B. In FIG. 10 a schematic structure of an assembly formed during incubation of multiple probe molecules B with a molecule A is shown. In this embodiment segment B1 is a component participating twice in the formation of a triplex and B2 is a component participating only once in this triple helix structure. An example for component B1 is PNA, while B2 can then be DNA. The sequence and orientation of the segments is chosen according to the principles laid down in FIGS. 2 and 3. It will be recognized that the longer the incubation time is, the larger the assembly grows and the more binding sites useful for the determination for example segments B2 are available, for example for binding a labeled secondary probe.

Figure 5A:
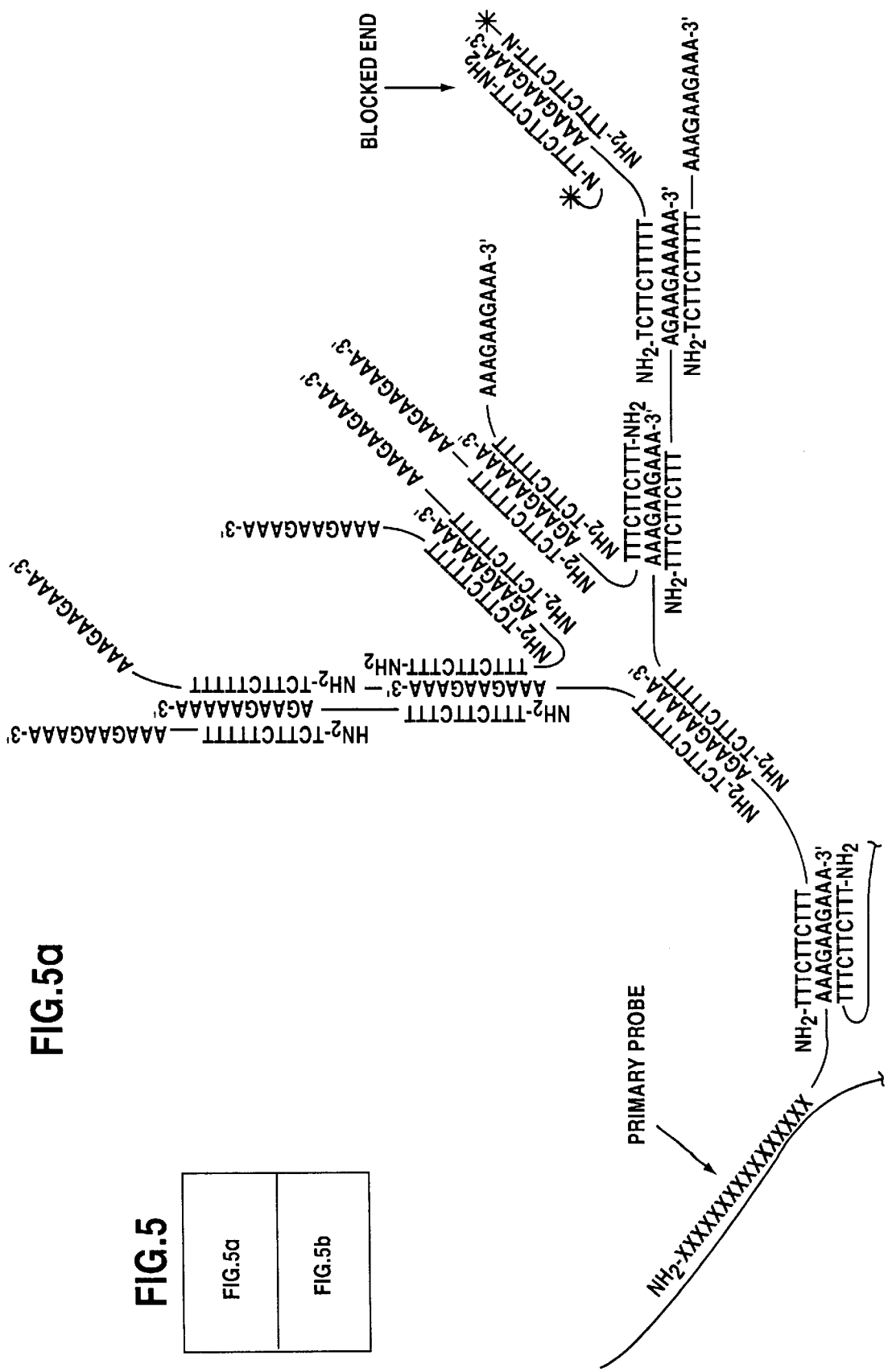
FIG. 5 gives a schematic picture of a construct formed in one of the exemplified methods according to the invention, wherein a target nucleic acid is analyzed using a primary probe, multiple probes composed of each a DNA and a PNA segment and secondary probes containing a reporter group, and having a blocked end that disables the probe in participating in further assembly. It shows that using the invention it is possible to obtain a multiplicity of labeling sites and therefore achieve signal amplification.
Figure 5B:
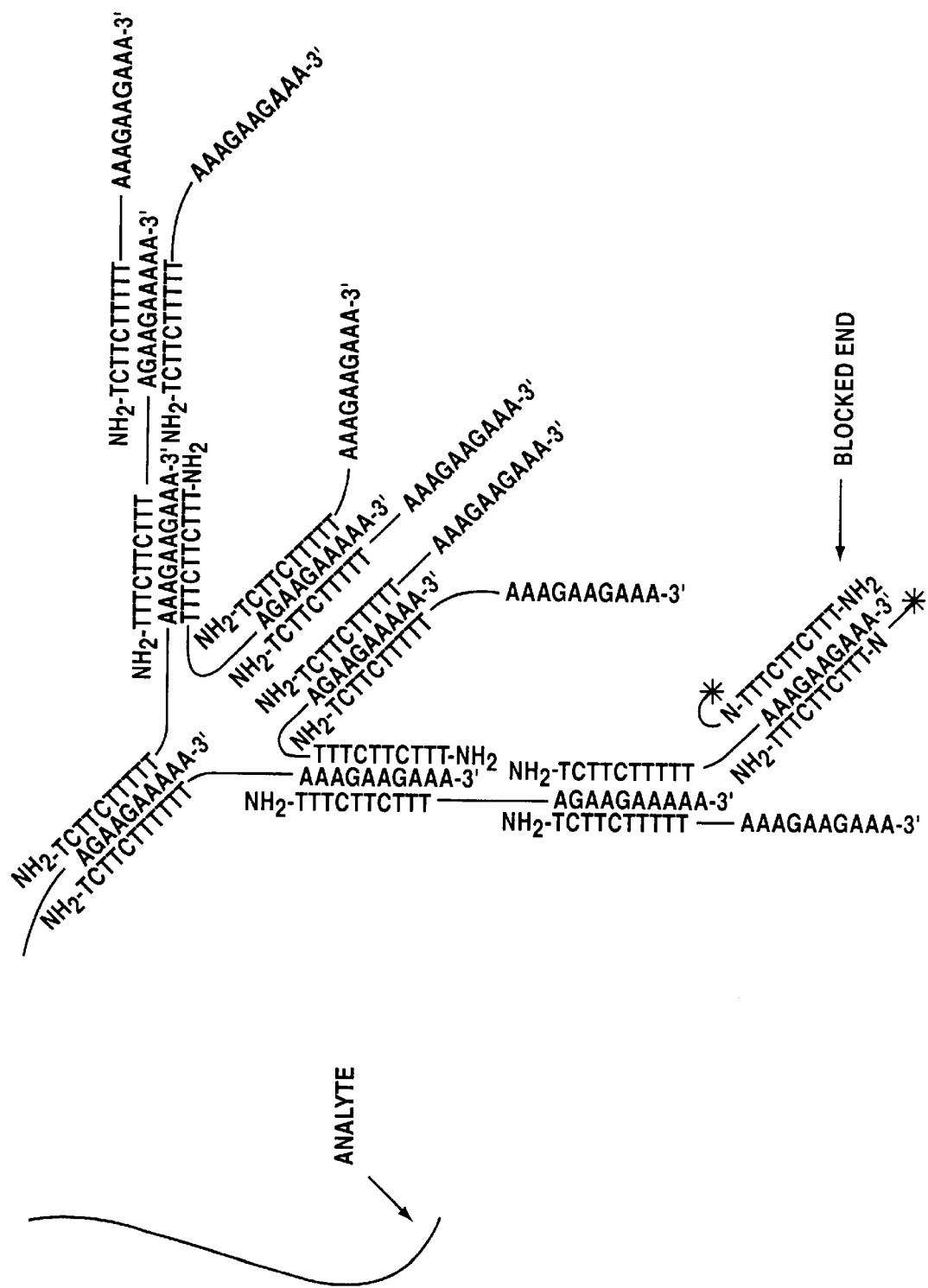

In a second embodiment which also uses chimera of one segment capable of occurring twice in triple helix structure and one segment occurring once in a triple helix structure, two kinds or probe molecules are used. These probe molecules differ in structure such that the sequences of segments 1 and 2 of each kind or probe are chosen such that these segments cannot form triple helices with the other segment of the same kind of probe. However, the second segment B2 of the first probe molecule B is capable of participating in triple helix structure with the first segment C1 of the second probe C and the second segment C2 of the second probe C can form a triple helix structure with the first segment B1 of a further probe molecule B. During incubation of these probe molecules with molecule A an assembly will be formed that contains a branched structure wherein the probe molecules are incorporated in an alternating way. Such a structure is shown in FIG. 5. FIG. 5 in addition shows that secondary probes containing a segment complementary to one of segments B2 or C2 of the probe molecules B or C can be incorporated to put a label on the assembly when the secondary probe acts as a terminator of the assembly process. The secondary probe should then not contain another segment complementary to any other segment of probe molecules B and C. This is named by the term blocked end. FIG. 5 further shows the formation of triplexes of different orientation, depending upon the sequence of the probe molecules.

As can be seen further, the segments preferably contain either purines or pyrimidines, such that one segment contains only purines, while the other contains only pyrimidines. This is preferred because highly stable triple helices form when pyrimidines of a PNA base pair to purines of a DNA using Watson/Crick binding and Hoogsteen binding.

The segments of the probe molecules can be synthesized independently, especially if the segments comprise different backbones. The synthesis of PNAs is described in WO 92/20702, whereas the synthesis of deoxyribonucleotides is possible according to a wide variety of methods, comprising chemical synthesis via phosporamidites or, especially for longer sequences, by methods including enzymes, like in the template dependent synthesis or restriction of double stranded nucleic acids. In a subsequent step the two segments are connected by the linker moiety L. The linker can be any molecular unit, such as amino acid residues, e.g., aspartate or glutamate, or other compounds like 8-aminodioxa-octanoic acid (Ado, according to DE-A-3943522) or hexamethylene.

In a third embodiment, which can involve both, duplex formation and triplex formation, there is used a first kind of probes containing first and second segments which occur twice in a triplex structure, whereas a second kind of probe molecules contains first and second segments that occur only once in triplex structures. In one example probe B contains two PNA segments and probe C contains two DNA segments. The sequence of segment C1 is such that it binds segment B2 and the sequence of segment C2 is chosen such that it binds sequence B1 of an additional molecule of probe B. Again, as outlined above, the sequences are chosen in sequence and symmetry such that the probes cannot bind intramolecularly and such that the overall sequence of probe B is not complementary to overall sequence of probe C. An assembly of those probes B and C leads to alternating assembly of the probes. The synthesis of such probes can be especially advantageous because they can be synthesized without interrupting automated chemical synthesis.

In case the assembly reaction involves four or more compounds (as in FIG. 6B), some compounds (for example compounds B and C as well as D and E or B, C and D or C, D, and E) may be combined and reacted prior to the overall mixing. Thus the duplex- or triplex-hybridisations may be conducted separately. Alternatively, each compound may be added stepwise, each step being succeeded by a washing step.

As described above for the chimeric molecules, it is possible to construct assemblies with more probes. An example of such a construct is given in FIG. 6B. In this case segment B2 of probe B is complementary to a segment C1 of probe C, segment C2 is complementary to a first segment D1 of a further kind of probe D, which in addition contains a segment D2 which is complementary to a first segment E1 of a further kind of probe molecule E, which in turn contains a segment E2 complementary to the sequence of segment B1. This assembly requires that for example segment C2 is not complementary to a segment B1 and D1 and segment C2 is not complementary to segment B1 and C1. In this way a controlled assembly of a multiplicity of probes using triple helix structures is possible.

The use of probe molecules containing only one kind of backbone in both segments has the advantage of easier synthesis of the probe molecules. The probe molecules can easily be synthesized totally from monomeric units without the need of a subsequent linkage step. If it is desired to use a linker connecting segments 1 and 2, or if an opposing orientation of the segments is chosen, it may be advantageous to synthesize the segments independently and connect them in a subsequent step as pointed out above.

A further subject of the invention is a molecule B containing a nucleobase sequence containing segments B1 and B2 wherein B1 contains a peptide bond containing backbone and B2 contains a natural backbone and wherein said segments are covalently bound together directly or through a linker moiety and wherein said binding is made between the amino terminus of B1 and the 3' terminus of B2 or the carboxylic acid terminus of B1 and the 5' terminus of B2. A peptide bond according to the invention is the chemical bond between a group CO and a group NR, wherein R is hydrogen or $C_2$–$C_6$ acyl or $C_1$–$C_6$ alky. A natural backbone contains sugar-phosphate units.

Figure 6A:
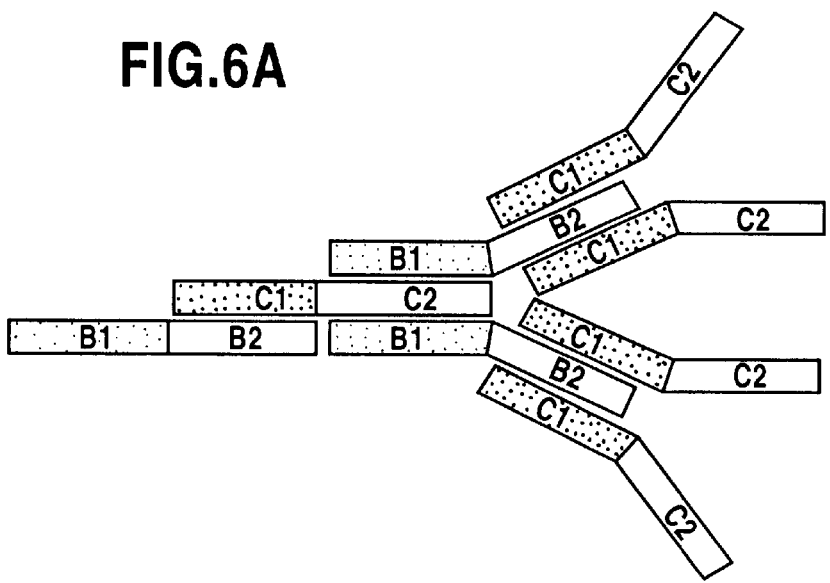
In FIG. 6A a schematic picture is shown for an exemplified embodiment of the invention using a first probe B containing two segments B1 and B2, and a second probe C containing two segments C1 and C2. The segments B1 and C1 consist of PNA and the segments B2 and C2 consists of DNA.
Figure 6B:
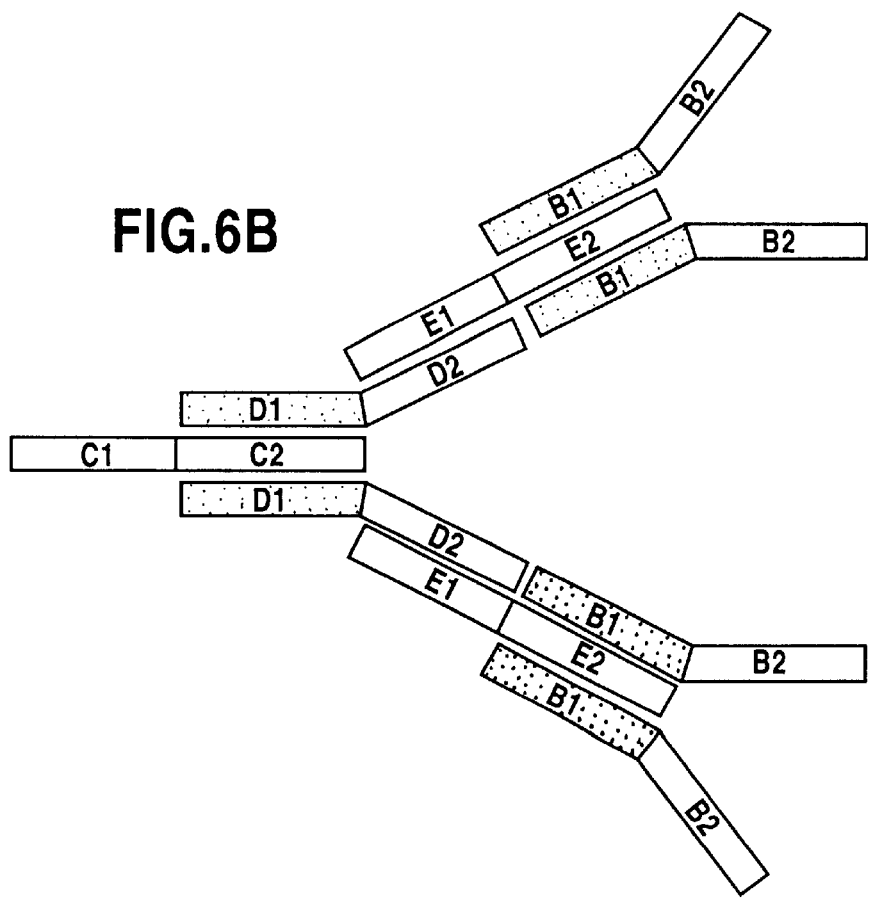
FIG. 6B shows the result of an assembly performed as in 6A but in the presence of four probes, termed B, C, D, and E containing two segments each. Both segments of probes C and E consist of DNA, and both segments of probes B and D consist of PNA.

A further subject of the invention is a method for the determination of an analyte comprising providing a reaction mixture containing a nucleobase SA containing molecule A, said molecule being capable of forming a triple helix structure through said sequence and being capable of binding to said analyte multiple probe molecules B containing a first segment B1 capable of participating in a triple helix structure with A through said sequence SA and a second segment B2 incubating said reaction mixture at conditions allowing the formation of triple helices and determining the formation of triple helices using said segment B2 as a measure for the analyte to be determined. Preferably the molecule A is a probe present in the reaction mixture in an amount dependent upon the presence/absence or amount of said analyte. An analyte according to this method is any molecule desired to be determined. Typical analytes are constituents of body fluids, for example blood or fluids derived therefrom, like serum or plasma, or urine or sputum. Some fluids require preparational steps to bring the analytes into accessible form. For example could it be required to lyse cell walls in order to release analytes. The analytes can be for example antibodies, antigens, haptens or nucleic acids. Nucleic acids are preferred analytes. In order to obtain a flexible system for universal amplification it is preferred to use a primary probe comprising a first segment of nucleobases complementary to the sequence of a stretch of the analyte sequence and a second segment which contains a nucleobase sequence complementary to segment B1. In this system the probe molecules can be used for analytes having different nucleobase sequences. A construct formed is shown in FIG. 6.

A further subject of the invention is the use of formation of multiple triple helix structures for the determination of an analyte.

A further subject of the invention is a composition of matter comprising a component N containing a sequence N1 capable of forming a triplex structure and a sequence N2 accessible for further hybridization and a component M containing a sequence M1 capable of forming a triplex structure including sequence N1 and a sequence M2 accessible for further hybridization. Examples of components N and M are molecule A and probe B or probe B and probe C. Those compositions of matter are intermediate products in the assembly of the above process. However, they can be used further to determine nucleic acids. An example of component O is probe D.

Principally, there are several options to define the chemical nature of molecules N, M and O in the present invention. They can be independently chosen from the group of nucleic acids, non-naturally occurring nucleic acid analogues and chimeras of nucleic acids and nucleic acid analogues. Non-naturally occurring nucleic acid analogues are those that while being capable of base pairing to nucleic acids, differ in structure from nucleic acids, preferably in the backbone. In these compounds the naturally occurring sugar phosphate backbone is replaced by a backbone containing subunits different from sugar and phosphate, preferably they contain at the least one peptide bond (CONH). Preferred examples are the compounds disclosed in WO 92/20702. Nucleic acids are DNA and RNA, preferably in the form of oligonucleotides. Chimeras are molecules containing both, a nucleic acid part and a nucleic acid analogue part, preferably connected at their ends, not excluding compounds containing more than one of these different parts. The parts can be linked together covalently by known methods, for example by activating one of the parts and reacting the activated compound with a compound of the other group having a group reactive with the activated site in the first compound. While the sequences N1, N2, M1 and M2 may be defined by the parts of the chimeras, this is not necessarily the case. The sequences N1, N2, M1 and M2 are more defined by their capabilities to bind to other nucleic acids or nucleic acid analogues, i.e. by their base sequences. These are chosen such that the required specificity for the reaction is achieved. In the following, some examples for sequences N1, N2, M1 and M2 are given. In a first case, N1 is a segment formed from a nucleic acid analogue, N2 is a DNA-part, M1 is a DNA-part and M2 is also a DNA-part. From the thus defined compounds N and M there will, under hybridizing conditions, be formed a complex containing one molecule N bound via a triplex structure containing two parts N1 and one part M1. In the bound status the part N2 and M2 can point into the same direction, can point into different directions or can point against each other. The configuration wherein the parts point into different directions will be preferred, as thus the binding capabilities of the parts N2 and M2 will be used optimal. The direction of binding can be influenced and determined by the actual sequences of N1 and M1. In a second case, N1 may be a nucleic acid analogue part and N2 may be a DNA part, and M1 may be a nucleic acid analogue part and M2 may be a DNA part. Then there may form a molecule comprising a duplex part formed by N1 and M1, the parts M2 and N2 preferably being free to form triplex structures with other molecules, preferably with nucleic acid analogues. One of those analogues may be a molecule O. If it is designed to participate in a triplex structure with two analogue parts, it will preferably be chosen to be a nucleic acid. It may be labelled by a detectable moiety, like a reporter group as known from diagnostics. The composition of matter of the present invention will contain 2 or more molecules, however, it can contain a large number of single molecules, like a agglomerate or composite, made up of many compounds N and M, and optionally containing other compounds like molecules O in a repetitive manner or arranged by chance. The composition can be used as a probe, especially, if the parts N2 of different molecules N have each a different sequence binding to adjacent segments of a nucleic acid, but also be the intermediate product of the above mentioned diagnostic method.

The following examples are given to exemplify the invention and determine conditions for successful conduction of the method:

GENERAL

The PNAs were synthesized according to WO 92/20702. If applicable, modifying groups are attached while the PNAs were still protected and on the solid phase. The PNAs had an amide function at the COOH end because of the choise of solid support and the subsequent way to decouple the PNA from the solid phase. Thus, in this case we denote the C-end with —$CONH_2$. The amino end is denoted —H. Monomers for synthesis of the PNAs were purchased from Millipore, USA. Oligonucleotides were synthesesized chemically on an automated synthesizer.

EXAMPLE 1

Analysis of Conditions for Triplex Formation

In order to estimate the of triplex forming capability of oligos (for example PNAs or probes B and c) melting temperature Tm was measured at pH 4.5 and 9.5, since no Hoogsteen base pairing is possible at the higher pH. In total, 1 ml of a solution containing 0.1 M phosphate buffer at the desired pH. Nine $\mu$M PNA and 4.5 $\mu$M DNA was heated to 95° C. for 10 min., and allowed to cool slowly at 22° C. for 18 h. Subsequently, 2 ml 0.1 M phosphate buffer at the relevant pH was added, and the optical density was measured ramping the temperature from 25° C. to 95° C. at 0.5° C./min. As can be seen from FIG. 12, Tm of segments B1 and C2 is 90° C. at pH 4.5, and 58° C. at pH 9.5. Such pH-dependency shows that Hoogsteen base pairing contributes significantly to the stability of the hybridisation complex, and that triplex formation has occurred.

The sequences of segments B1 (PNA) and C2 (DNA) are
B1: Ac-glu-Ado-TTTCTTCTTT-$CONH_2$
C2: $NH_2$-$(CH_2)_6$-5'-AAAGAAGAAA-3' (SEQ.ID.NO. 1)

EXAMPLE 2

Synthesis of DNA-PNA Chimera

A DNA oligo with a six-carbon atom (hexamethylene) linker and a terminal, was linked to a PNA oligo with glutamate residue at the amino terminus, i.e., the DNA oligo SIG1 with PNA187 and the DNA oligo SIG2 with PNA184. The reaction mixture was as follows:

5 $\mu$l DMSO

2 $\mu$EDC, 0.5 M

2 $\mu$l imidazole, 1 M 3.6 nmol PNA (PNA187 or PNA184)

3.6 nmol DNA (SIG1 or SIG2)
H$_2$O to 20 μl
where:
SIG1: 5' NH$_2$-(CH$_2$)$_6$-AAAGAAGAAA3' (SEQ.ID.NO. 1)
SIG2: NH$_2$-(CH$_2$)$_6$-5'-AAGAGAAAAA-5' (SEQ.ID.NO. 2)
PNA187: Ac-Glu-Ado-TTTCTTCTTT-CONH$_2$
PNA197: Ac-Glu-Ado- TTTTTCTCTT-CONH$_2$
Ac means Acetyl The reaction proceeded at 22° C. for 1–5 days.

Chimera with the following sequences were produced:
NH$_2$CO-TTTCTTCTTT-AAGAGAAAAA-3'
NH$_2$CO-TTCTCTTTTT-AAAGAAGAAA-3'

The DNA was labelled with $^{32}$P-ddATP by convential enzymatic terminal elongation.

EXAMPLE 3

Analysis of Chimera by Gel Chromatography

After reaction, 30 μl was added 5 μl 80% formamide, heated to 95° C. for 5 min., cooled on wet ice for 10 min., and applied a 12% denaturing polyacrylamide gel.

18 ml 20% gelmix
10.8 ml 8% urea
1.2 ml 10×TBE (0.9 M Tris-borate, 0.01 M EDTA)
300 μl APS (ammonium per sulphate)
10 μl TEMED (N,N,N',N'-tetramethylethylene diamine)
where 20% gelmix consists of 7 M urea, 90 mM tris-borate pH 8.3 and 0.67% bisacrylamid. Electrophoresis was performed for 60 min. at 400 V. After electrophoresis the gel was wrapped in polyethylene film, placed on TLC plate, subjected to UV light and photographed. A reaction product was observed with approximately half the migration rate the DNA oligos.

EXAMPLE 4

Purification of Chimera

After electrophoresis, a gel fragment containing the chimera was excised from the gel, washed in 1 ml TE Buffer for 5 min., subsequently placed into 200 μl TE pH 8.3, and extracted with vigorous shaking overnight at 55° C.

EXAMPLE 5

Formation of Assemblies for Signal Amplification

In order to show that complexes of DNA with PNA can be formed wherein both, a part of the DNA and a part of the PNA is accessible for binding further probe molecules, the following PNA and DNA molecules were incubated:

DA256:5'-CGACTTCAGCATGACTCAAAGAAGAAA-3' (SEQ.ID.NO. 3)
DA262: 5'-ATGTGGACATTGTCATCAAGAAAAGAA-3' (SEQ.ID.NO. 4)
PNA380: Ac-Glu-TGACAATGTCCACAT-Ado-Glu-Ado-Glu-Ado-TTTCTTCTTT-Glu-NH$_2$
PNA414: Ac-Glu-GTCATGCTGAAGTCG-Ado-Glu-Ado-Glu-Ado-TTCTTTTCTT-Glu-NH$_2$
DA256*: DA256 labelled with $^{32}$P-dATP and oligonucleotide kinase.

Figure 12:
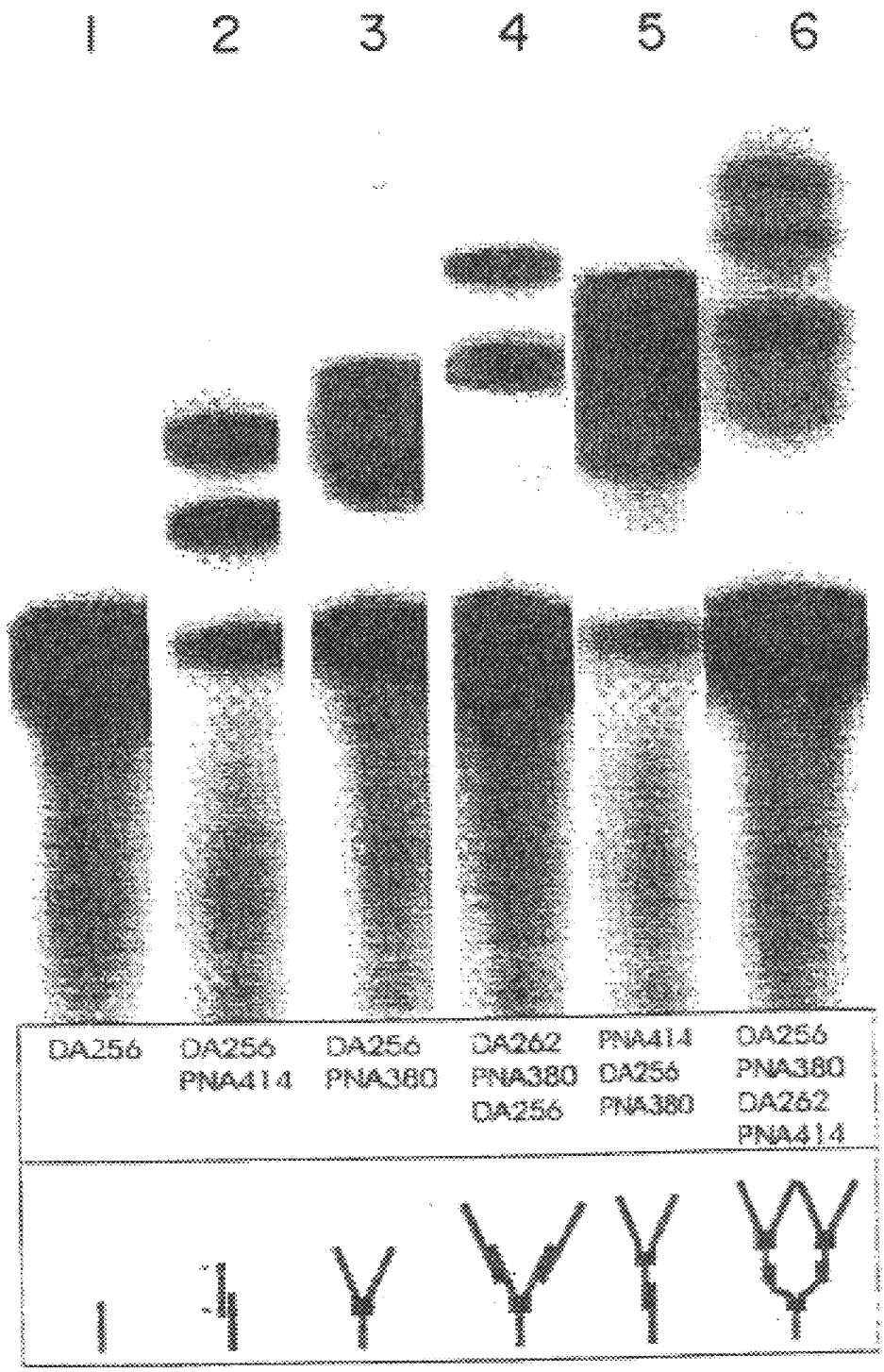
FIG. 12 shows an autoradiogram showing the different starting compounds and reaction products for the formation of duplexes and triplexes.

The results are shown in FIG. 12.

Experiment 1

This is just the preparation of a solution containing 1 pmol DA256* (see lane 1).

Experiment 2

In this experiment 1 pmol DA256* and 10 pmol PNA414 were mixed in 10 μl water and incubated overnight (see lane 2).

Experiment 3

In this experiment 1 pmol DA256* and 10 pmol PNA380 were incubated. This experiment yields a DNA having two PNAs bound via triplex formation. This is the first molecule that can be used as a probe in nucleic acid hybridisation assays, if the part of the DNA not participating in the triplex formation is complementary to a selected region of a target nucleic acid. Instead of one binding side, now two binding sites (the free accessible parts of the PNAs) have been created (see lane 3).

Experiment 4

In this experiment two DNA molecules (1 pmol DA256* and 20 pmol DA262) are incubated together with 10 pmol PNA380. This experiment shows that the binding sides remaining on the PNA380 further react with DNA molecules of complementary sequence forming duplexes. This can be seen from lane 4 of FIG. 12, wherein the complex formed as seen in lane 3 disappears in favour of higher molecular weight bands.

Experiment 5

This experiment shows that also the DNA part of DA256 is accessible to hybridisation with a PNA molecule, forming a duplex. In this experiment 1 pmol DA256*, 5 pmol PNA414 and 10 pmol PNA380 are mixed and incubated overnight. In lane 5 of FIG. 5 it can be seen that, compared to lane 3, there is formed a higher molecular weight complex, indicating additional duplex formation with PNA414.

Experiment 6

In this experiment all four probes were mixed together to create very high molecular weight assemblies. 1 pmol DA256*, 9 pmol DA256, 10 pmol DA262, 10 pmol PNA380 and 10 pmol PNA414 are mixed and incubated overnight. As can be seen from lane 6 of FIG. 13 high molecular weight structures have formed. This is the first indication that the binding sites of originally 1 probe is enhanced four times. The conditions for running the gel of FIG. 12 is 12% polyacrylamid with the buffer of TAE pH 7.0.

EXAMPLE 6

Formation of an Assembly Having Doubled Binding Sites

This experiment shows the formation of the complex containing a first probe (DA256) binding via triplex formation to further probes (PNA380), which bind via duplex formation one further probe (DA262) each. The sequences of the oligomers used are given in Example no. 6. The conditions are the following:
Samples 1–7 contain:
1 pmol DA 256*
9 pmol DA256
40 pmol PNA380
X pmol PNA262 (X=0; 1; 5; 10; 20; 40; 100)
Gel: 12% Polyacrylamid
Buffer: TAE pH 7.0

Figure 13:
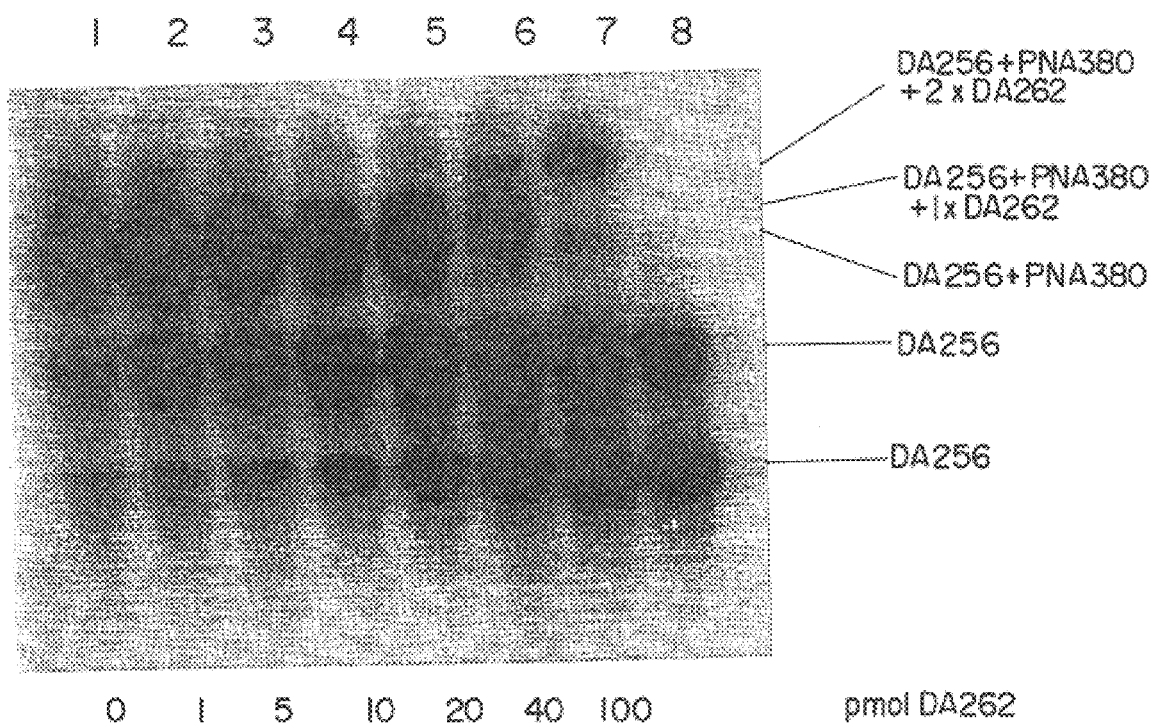
FIG. 13 shows an autoradiogram for the formation of a complex involving duplexes and a triplex, wherein the amount of the only duplex forming oligonucleotide is increased from lane 1 to lane 7 (0; 1; 5; 10; 20; 40; 100 pmol DA262). Lane 8 contains only the triplex forming component DA256.

The results are presented in FIG. 13. The lanes correspond to the samples as given above. It can be seen with lower concentrations of DA262 there is formed predominant an assembly of DA256 and PNA380 having a higher molecular weight than DA256. With increasing amount of DA262 there is formed a higher molecular weight complex (especially lanes 6 and 7). In lane 7 the predominant product is the complex containing one triplex structure and two duplex structures.

We claim:

1. A method of detecting a molecule A containing a nucleobase sequence SA, the method comprising:
   (a) providing a reaction mixture containing the molecule A, containing the nucleobase sequence SA in single-stranded form, and a plurality of single-stranded probe molecules B, each of which comprises a nucleobase sequence B1 linked to a nucleobase sequence B2, which nucleobase sequence B2 does not directly base pair with the nucleobase sequence SA,
      wherein two nucleobase sequences B1 hybridize with the nucleobase sequence SA, to form a triple helix structure; and
   (b) directly or indirectly detecting the nucleobase sequence B2, thereby detecting the molecule.

2. The method of claim 1, wherein the nucleobase sequence SA is at least 9 bases in length.

3. The method of claim 1, wherein the nucleobase sequence SA is 10 to 30 bases in length.

4. The method of claim 1, wherein the nucleobase sequence B1 consists of a peptide nucleic acid.

5. The method of claim 1, wherein step (a) comprises
   providing a reaction mixture containing the molecule A and a plurality of single-stranded probe molecules B, each of which comprises a nucleobase sequence B1 linked to a nucleobase sequence B2, which nucleobase sequence B2 does not directly base pair with the nucleobase sequence SA,
   wherein any two nucleobase sequences B1 hybridize with the nucleobase sequence SA or one nucleobase sequence B2, to form a branched structure comprising a plurality of triple helix structures, one of which is comprised of the nucleobase sequence SA and two nucleobase sequences B1, and the remainder of which are comprised of one nucleobase sequence B2 and two nucleobase sequences B1.

6. The method of claim 1, wherein step (b) comprises hybridizing to the nucleobase sequence B2 a labeled probe comprising a sequence which is complementary to the nucleobase sequence B2 and a label and thereafter detecting the label.

7. The method of claim 6, wherein no further nucleobase sequence which is complementary to a sequence contained in the reaction mixture is present on the labeled probe.

8. The method of claim 6, wherein the amount of labeled probes is provided in the reaction mixture in step (a), and the amount of the labeled probes in the reaction mixture is less than the amount of the probe molecules B in the reaction mixture.

9. The method of claim 6, wherein the amount of labeled probes is provided in the reaction mixture in or after step (a), and the amount of the labeled probes in the reaction mixture is more than the amount of probe molecule B which contains the nucleobase sequence B2 in the reaction mixture available for detecting in step (b).

10. A method of detecting a molecule A containing a nucleobase sequence SA, the method comprising:
    (a) providing a reaction mixture containing the molecule A containing nucleobase sequence SA in single-stranded form,
    a plurality of single-stranded probe molecules B, each of which comprises a nucleobase sequence B1 linked to a nucleobase sequence B2,
    a single-stranded primary probe, comprising a nucleobase sequence X linked to a nucleobase sequence B2 which has the same sequence as the nucleobase sequence B2 of the probe molecule B, wherein the nucleobase sequence X hybridizes with the nucleobase sequence SA, and
    a plurality of probe molecules C, each of which comprises a nucleobase sequence C1 linked to a nucleobase sequence C2,
       wherein any two nucleobase sequences C1 hybridize with one nucleobase sequence B2 to form a triple helix structure, and any two nucleobase sequences B1 hybridize with one nucleobase sequence C2 to form a triple helix structure, to form a branched structure comprising a plurality of triple helix structures; and
    (b) directly or indirectly detecting the nucleobase sequence B2 or the nucleobase sequence C2, thereby detecting the molecule A.

11. The method of claim 10, wherein step (b) comprises hybridizing to the nucleobase sequence B2 or the nucleobase sequence C2 a probe comprising a sequence which is complementary to the nucleobase sequence B2 or the nucleobase sequence C2, respectively, and a label, and thereafter detecting the label.

12. The method of claim 10, wherein the nucleobase sequence B1 and the nucleobase sequence C1 each consist of peptide nucleic acid, and the nucleobase sequence B2 and the nucleobase sequence C2 each consist of DNA.

13. A method for determining an analyte in a reaction mixture, the method comprising:
    (a) providing a reaction mixture containing the analyte to be determined,
    a molecule A, comprising a segment which is linked to a nucleobase sequence SA, wherein the segment binds to the analyte, and
    a plurality of single-stranded probe molecules B, each of which comprises a nucleobase sequence B1 linked to a nucleobase sequence B2, which nucleobase sequence B2 does not directly base pair with the nucleobase sequence SA,
       wherein two nucleobase sequences B1 hybridize with the nucleobase sequence SA, to form a complex comprising the analyte attached to a triple helix structure; and
    (b) directly or indirectly detecting the nucleobase sequence B2, thereby detecting the analyte.

14. The method of claim 13, wherein the analyte is a nucleic acid.

15. The method of claim 14, wherein the segment is a nucleobase sequence which is complementary to at least a portion of the analyte.

16. A composition of matter, comprising a molecule N comprising a nucleobase sequence N1 linked to a nucleobase sequence N2, and two molecules M, each of which comprises a nucleobase sequence M1 linked to a second nucleobase sequence, in which second nucleobase sequence is not directly base paired with the nucleobase sequence N1, wherein the second nucleobase sequence is the same or different on each of the two molecules M, wherein each of the two nucleobase sequences M1 is hybridized with the nucleobase sequence N1, to form a triple helix structure.

17. The composition of matter of claim 16, wherein the nucleobase sequence N2 is not directly base paired to the second nucleobase sequence.

18. The composition of matter of claim 16, wherein the second nucleobase sequence different on each molecules M.

19. The composition of matter of claim 16, further comprising a molecule O which is bound to the nucleobase sequence N2 or the second nucleobase sequence.

20. The composition of matter of claim 16, further comprising two molecules O, each of which is bound to one of the second nucleobase sequences.

21. The method of claim 1, wherein, before step (b), the triple helix structure is separated from unreacted components of the reaction mixture.

22. The method of claim 10, wherein, before step (b), the branched structure is separated from unreacted components of the reaction mixture.

23. The method of claim 13, wherein, before step (b), the complex is separated from unreacted components of the reaction mixture.

* * * * *